(12) United States Patent
Kaneblei

(10) Patent No.: US 8,377,709 B2
(45) Date of Patent: Feb. 19, 2013

(54) DEVICE AND PROCESS FOR THE CHROMATOGRAPHIC DETECTION OF A SUBSTANCE

(75) Inventor: Ingo Kaneblei, Herrnburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 582 days.

(21) Appl. No.: 12/370,862

(22) Filed: Feb. 13, 2009

(65) Prior Publication Data

US 2009/0253213 A1   Oct. 8, 2009

(30) Foreign Application Priority Data

Apr. 2, 2008  (DE) .................. 10 2008 016 763

(51) Int. Cl.
*G01N 30/90* (2006.01)
(52) U.S. Cl. .......... 436/162; 436/164; 436/169; 422/50; 422/68.1; 422/82.05; 422/82.06
(58) Field of Classification Search ............... None
See application file for complete search history.

(56) References Cited

U.S. PATENT DOCUMENTS

| | | | |
|---|---|---|---|
| 5,089,232 A | 2/1992 | May | |
| 2002/0132363 A1* | 9/2002 | Rehm | ........................... 436/164 |
| 2007/0081920 A1 | 4/2007 | Murphy et al. | |

FOREIGN PATENT DOCUMENTS

| | | |
|---|---|---|
| CA | 2243801 | 5/1999 |
| DE | 39 02 402 | 6/1990 |
| DE | 195 12 374 | 10/1996 |
| DE | 197 51 363 | 6/1999 |

OTHER PUBLICATIONS

Thin -Layer Chromatography, retreived online from http://web.archive.org/web/20050420000817/http://www.wpi.edu/Academics/Depts/Chemistry/Courses/General/tlc.html.*
Michael von Gahlen; Draeger Safety AG & Co. KGaA; Draeger Drug Test, Modern Equipment for Police Forces; 8th European Police Congress; Apr. 6 and 7, 2005.
Draeger Safety AG & Co, KGaA; Draeger Drug Test; Gasmess-Technik Draeger Drugtest; Vorabdruck Aus Dem Draegerheft 377; Apr. 2004; pp. 1-8.

* cited by examiner

*Primary Examiner* — Robert Xu
(74) *Attorney, Agent, or Firm* — McGlew and Tuttle, P.C.

(57) ABSTRACT

A device for the chromatographic detection of a substance provides an improved reproducible measuring process. A monitoring indicator (6) is provided, which is designed to detect the relative position of a test strip (13) in relation to the direction of the force of gravity, wherein a processor unit (8) generates a shut-off signal or interruption signal for the process control system (7) if a limit value is exceeded.

5 Claims, 4 Drawing Sheets

DEVICE AND PROCESS FOR THE CHROMATOGRAPHIC DETECTION OF A SUBSTANCE

CROSS REFERENCE TO RELATED APPLICATIONS

This application claims the benefit of priority under 35 U.S.C. §119 of German Patent Application DE 10 2008 016 763.0 filed Apr. 2, 2008, the entire contents of which are incorporated herein by reference.

FIELD OF THE INVENTION

The present invention pertains to a device for the chromatographic detection of a substance.

BACKGROUND OF THE INVENTION

A sampling and analysis system for detecting substances is known from DE 197 51 363 B4. A test strip with a collection matrix and with a detection matrix is exposed to the analyte to be detected. After conclusion of the phase of collection, the analyte is reacted with a binding partner in a one-step process by adding a developer solution and the presence or absence of the analyte in the detection matrix is displayed. The prior-art analysis system is an immunochromatographic detection reaction, in which the detection reaction can be read and analyzed via an optical aperture.

Users frequently wish to carry out the analysis of the test strip automatically, because it may be difficult at the site of measurement to perform the individual analysis steps in the correct sequence in time and with precision. A sampling and analysis system with automated chromatographic analysis of a chip-like detection system by means of an optoelectronic scanning device is disclosed, for example, in DE 39 02 402 C1.

The individual measuring channels of the detection system are brought by means of transport rollers into the range of action of the optoelectronic scanning device in order to make it possible to perform a longitudinal scanning in the individual colored measuring channels. Since the detection reagent reacts in the channels directly with the substance to be detected during the measurement, the color reaction that becomes established can be analyzed directly. If, however, a developer solution is needed for the detection reaction, it may happen that this cannot be distributed uniformly within the test strip when the analysis is carried out, in addition, in a measuring device housing that is closed towards the outside. The consequence of this is that the measurement results may vary and greater measuring uncertainties will arise.

SUMMARY OF THE INVENTION

A basic object of the present invention is to improve a device of the type described above in terms of a reproducible measuring process and to propose a process herefor.

According to the invention, a device is provided for the chromatographic detection of a substance. The device comprises a test strip provided with a detection reagent for detection of the substance, an optoelectronic scanning system for optoelectronically scanning the test strip and a reservoir containing developer fluid for penetration into the test strip to bring about a detection reaction. A process control system is provided for exposure of the test strip to the developer fluid and for analysis of the detection reaction with the optoelectronic scanning system. A monitoring indicator is provided for detecting the relative position of the test strip in relation to the direction of the force of gravity or the relative motion in relation to a fixed reference point in space. A processor unit generates a shut-off signal or interruption signal for the process and for the control system if a limit value is exceeded.

The monitoring indicator may comprise an inclination sensor. The monitoring indicator may comprise an acceleration sensor.

According to another aspect of the invention, a process is provided for the chromatographic detection of a substance. The process comprises providing a device comprising a test strip with a detection reagent, a measuring device with an optoelectronic scanning system for the test strip and a reservoir containing developer fluid for penetrating into the test strip to bring about a detection reaction. The test strip is exposed to the substance to be detected and is inserted it into the measuring device. The test strip is exposed to the developer fluid. The relative position of the test strip is detected in relation to the direction of the force of gravity or the relative motion in relation to a fixed reference point in space with a monitoring indicator. The analysis operation is interrupted or terminated when the measured signal of the monitoring indicator exceeds a preset limit value.

The advantage of the present invention is that the relative position of the test strip relative to the direction of the force of gravity or the relative motion of the test strip in relation to a fixed reference point in space is determined with a monitoring indicator and the analysis operation is interrupted or even terminated altogether when a permissible range is exceeded. The monitoring indicator may also detect the relative position and relative motion in a combination and send corresponding measured signals to the processor unit. An inclination sensor, which detects whether the measuring device is aligned in the horizontal position, is preferably used as the monitoring indicator.

Inclination sensors that are arranged at a monitoring housing are known from the state of the art and are disclosed, for example, in DE 195 12 374 C2. Outer electrodes arranged concentrically to one another and a central electrode, between which a conductive liquid is present, are provided in a sensor housing. The conductivity values between the outer electrodes and the central electrode change depending on the position of the liquid level, and analysis of the inclination in both the longitudinal direction and transverse direction is possible.

The inclination sensor is preferably arranged on the housing of the measuring device or it is located in the vicinity of the test strip or on a printed circuit board connected to the housing, so that it can monitor the horizontal alignment of the test strip within the measuring housing. The inclination sensor sends measured signals, which are continuously analyzed by the processor unit of the measuring device, and a comparison with permissible limit values is performed as well, exceeding of a limit value is displayed to the user via a display unit and the user is prompted to check the alignment of the measuring device. If no correction is made, the processor unit generates a shut-off or interruption signal in order to stop or completely terminate the measuring process. Two sensors are especially preferably provided for detecting the inclination for each axis in space.

Arranging a mechanical inclination sensor in the form of a bubble level in addition to the inclination sensor arranged internally is within the scope of the present invention. This has the advantage for the user that he or she can be convinced of the proper alignment of the measuring device immediately before the start of the measurement.

The process described according to the present invention comprises the exposure of a test strip to the substance to be detected, subsequent introduction of the test strip into the detection device, exposure of the test strip to the developer fluid, detection of the relative position of the test strip in relation to the direction of the force of gravity or the relative motion in relation to a fixed reference point in space with a monitoring indicator, and interruption or termination of the analysis operation when the measured signal of the monitoring indicator exceeds a preset limit value.

An exemplary embodiment of the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
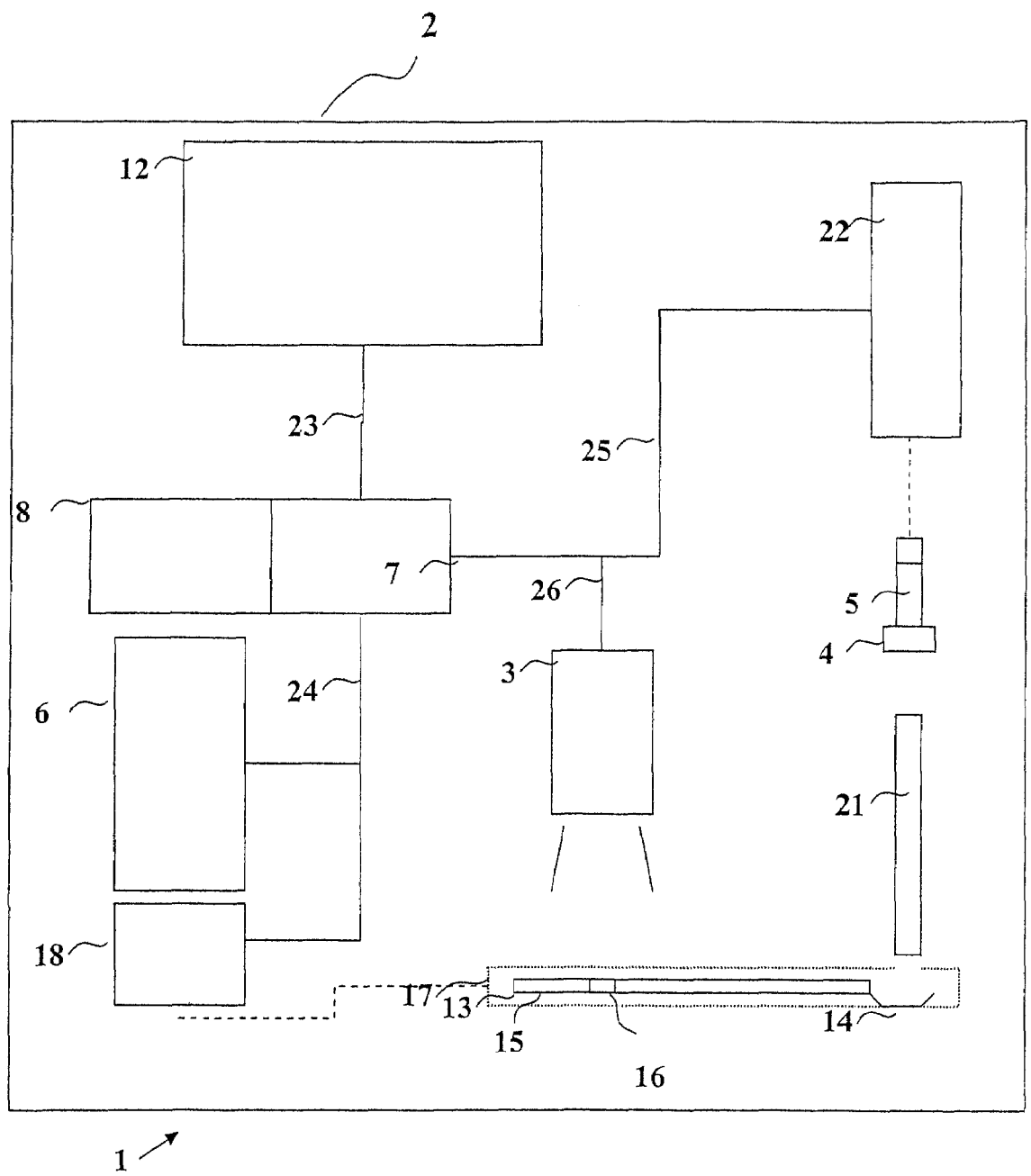
FIG. 1 is a schematic view showing the design of a measuring device according to the present invention.
Figure 2:
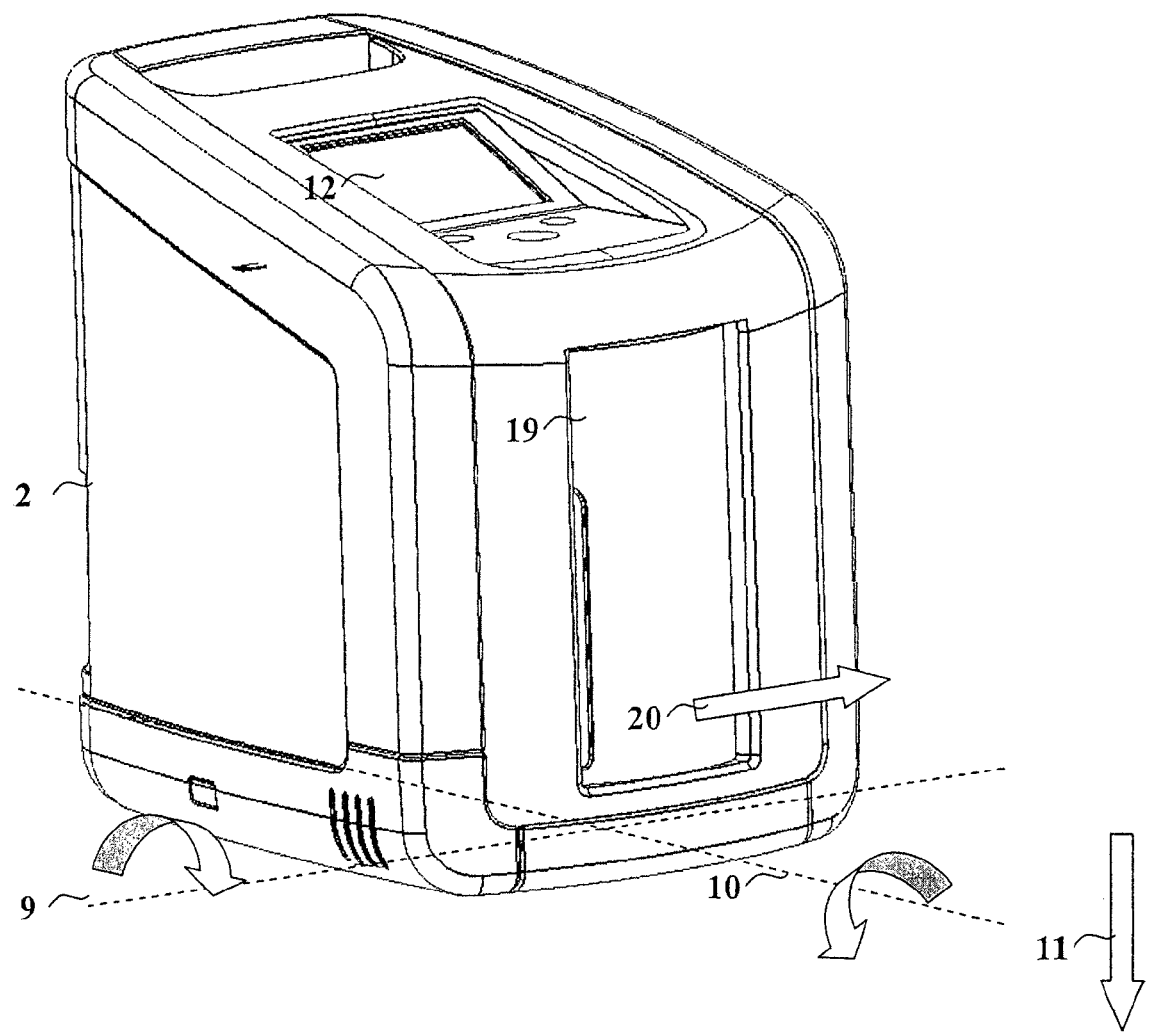
FIG. 2 is a perspective view showing the measuring device according to the invention.

Referring to the drawings in particular, FIG. 1 schematically illustrates the design of a measuring device 1 according to the present invention for the chromatographic detection of a substance. An optoelectronic scanning system 3, a reservoir 4 containing a developer fluid 5, an inclination sensor 6 and a process control system 7 forming one assembly unit with a processor unit 8 are arranged in a measuring device housing 2. The inclination sensor 6, acting as a monitoring indicator for the horizontal alignment of the measuring device 1, is arranged on the inside of the measuring device housing 2 and detects the inclination of the measuring device housing 2 both in the longitudinal direction 9 and the transverse direction 10 in relation to an axis 11 of the force of the gravity, FIG. 2.

Figure 3:
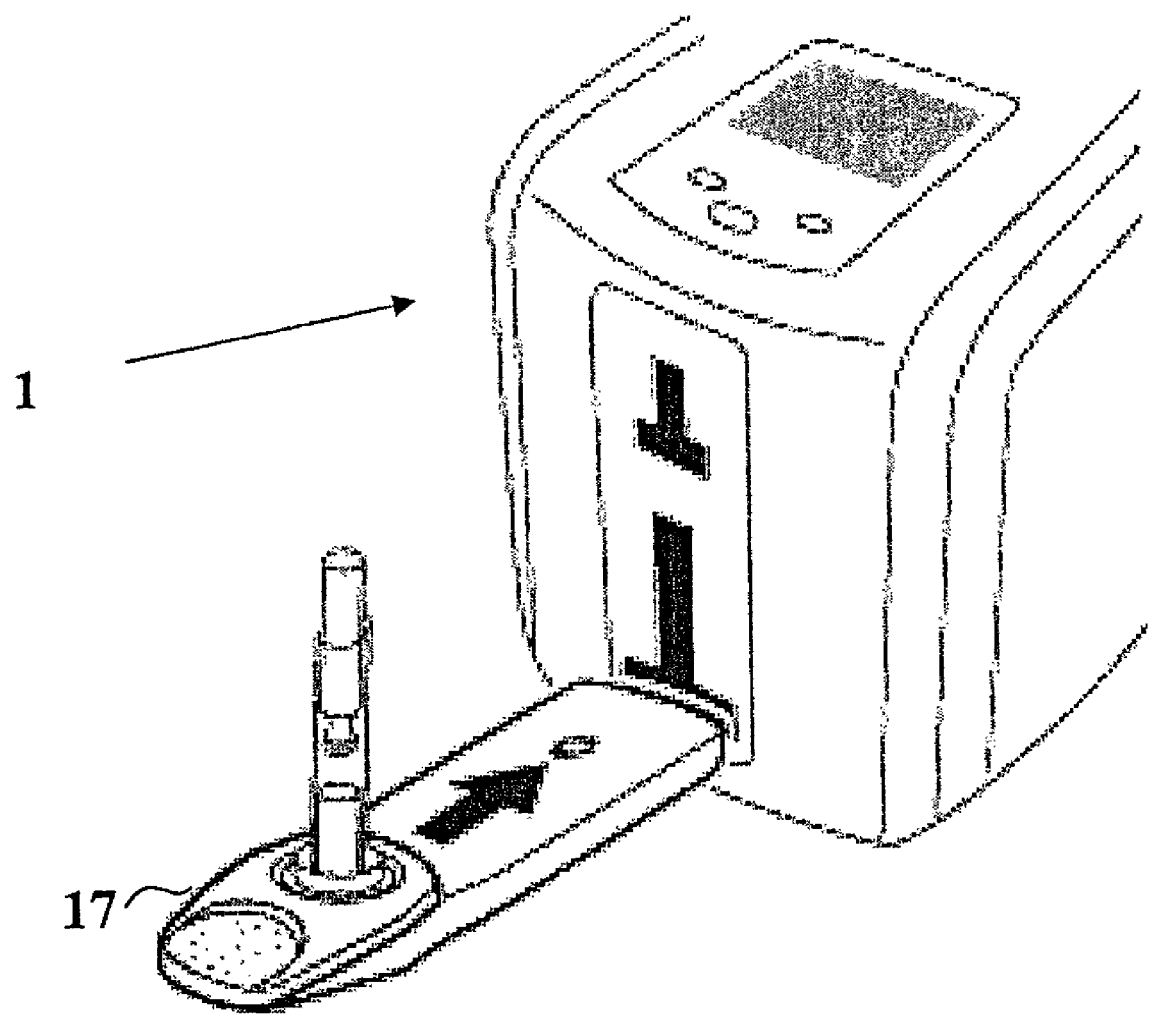
FIG. 3 is a perspective view showing a cassette before it is pushed into the measuring device.

A display unit 12 for outputting measured data, status and warning reports is located on the front side of the measuring device housing 2. A test strip 13, which comprises a collection matrix 14, a detection matrix 15 with a reagent 16 and a cassette 17 accommodating the collection matrix 14 and the detection matrix 15, is located under the optoelectronic scanning system 3, FIG. 3.

The cassette 17 is guided on transport rollers, not shown in greater detail, within the measuring device housing 2. To introduce the test strip 13 into the measuring device housing 2, a housing flap 19 is pivoted laterally along arrow 20 and the cassette 17 is pushed in, FIG. 2. A mechanism 18 moves the test strip 13 relative to the scanning system 3 in order to achieve scanning resolved in space.

The collection matrix 14 was exposed before to the sample to be analyzed during a sampling. The reservoir 4 is closed by a membrane, not shown in greater detail, and moved by a motor-driven feeding system in the form of an actuator 22 such that the membrane is pierced. The developer fluid 5 can then empty into the area of the collection matrix 14 via a fluid line 21. The substance to be detected is transported into the detection matrix 15 by means of the developer fluid 5 by capillary action. The actuator 22, inclination sensor 6, display unit 12 and optoelectronic scanning system 3 are connected to the process control system 7 via data lines 23, 24, 25, 26.

After the cassette 17 with the test strip 13 has been introduced into the measuring device 1, the reservoir 4 is first opened by the actuator 22 and the collection matrix 14 is provided with developer fluid 5. The inclination sensor 6 now monitors whether the measuring device housing 2 is aligned such that the developer fluid 5 can be distributed uniformly. The measured signals of the inclination sensor 6 are compared for this with limit values, and the processor unit 8 generates a shut-off or interruption signal for the process control system 7 if the limit value is exceeded. Deviations in both the longitudinal direction 9 and transverse direction 10 are detected with the inclination sensor 6, and the directions of rotation are illustrated by arrows, FIG. 2.

Figure 4:
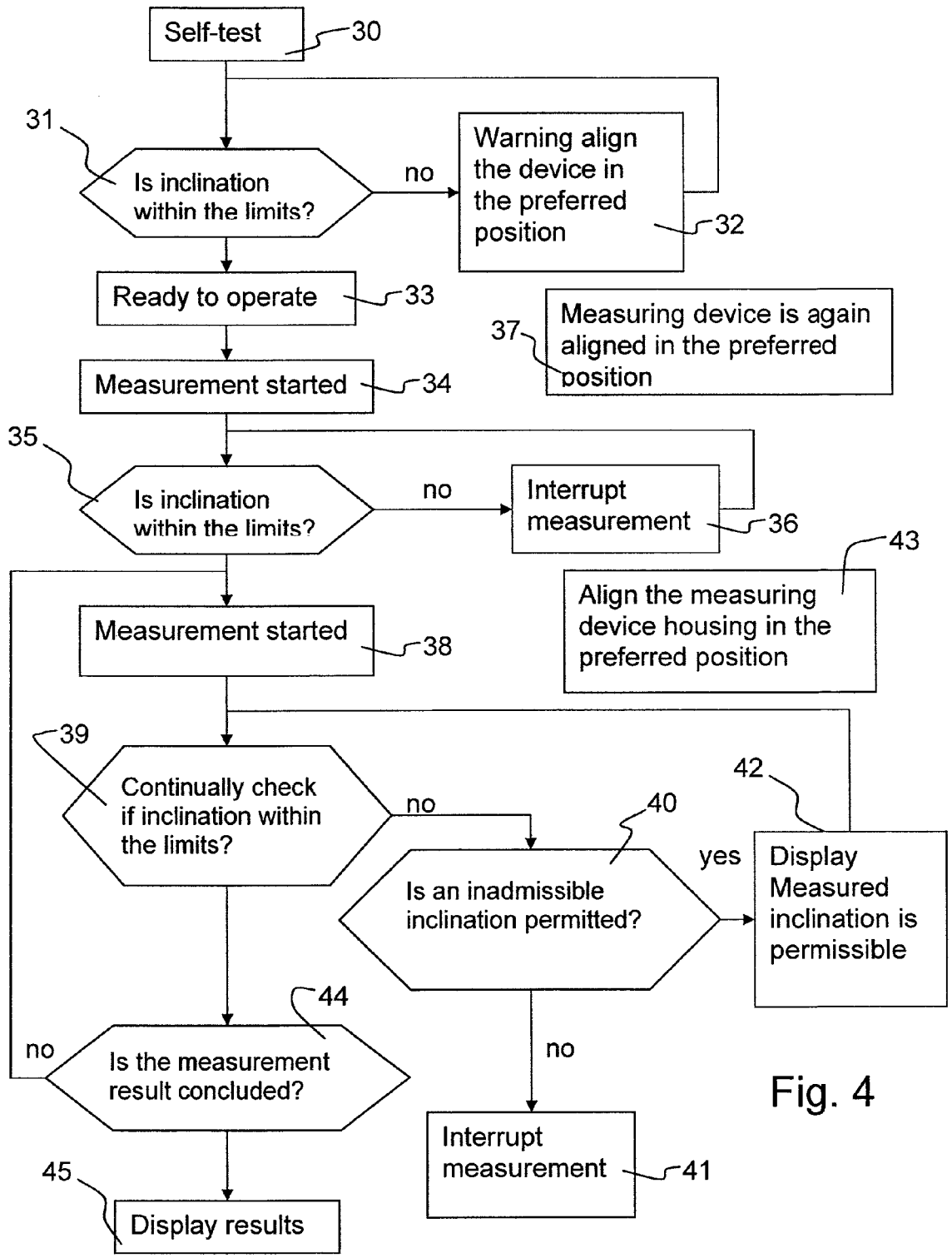
FIG. 4 is a flow diagram showing an exemplary measuring process according to the present invention.

FIG. 4 schematically illustrates the measuring process of the measuring device 1.

A self-test of the measuring device 1 is carried out at first in a step 30. Whether the inclination of the measuring device housing 2 is within the specified limits is then checked in step 31. If the tolerance limit is exceeded, a warning is sent via the display unit 12 in step 32 to align the device in the preferred position. If the device is ready to operate in step 33, the measurement is started in step 34. The inclination is checked again in step 35. The measurement is interrupted in step 36 in case the limit value is exceeded until the measuring device 1 is again aligned in the preferred position, step 37, and the user receives a corresponding message via the display unit 12. The inclination is checked continually in step 39 during the measurement process in step 38. The measurement is interrupted, steps 40, 41, if the status of measurement does not permit an inadmissible inclination. If the measured inclination is permissible during the process step, the user receives a message about this via the display unit 12 in step 42 to align the measuring device housing 2 in the preferred position, step 43. After conclusion of the measurement in step 44, the measurement result is outputted via the display unit 12, step 45.

While specific embodiments of the invention have been shown and described in detail to illustrate the application of the principles of the invention, it will be understood that the invention may be embodied otherwise without departing from such principles.

What is claimed is:

1. A device for the chromatographic detection of a substance, the device comprising:
   a housing with a test strip area;
   a test strip provided with a detection reagent for detection of the substance;
   an optoelectronic scanning system for optoelectronically scanning the test strip, the optoelectronic scanning system being supported by the housing;
   a reservoir containing developer fluid for penetration into the test strip to bring about a detection reaction, the reservoir being supported by the housing for providing developer fluid from the reservoir to the test strip area;
   a process control system connected to an actuator for opening the reservoir and connected to the optoelectronic scanning system for exposure of the test strip to the developer fluid by controlling emptying of the reservoir to provide developer fluid from the reservoir to the test strip area and for analysis of the detection reaction with the optoelectronic scanning system;

an inclination sensor for detecting the orientation of the housing with the test strip area with respect to a direction of the force of gravity and generating a measurement signal, the inclination sensor being connected to the process control system; and a processor unit connected to the process control system for generating a shut-off signal or interruption signal for the process control system from the measurement signal of the inclination sensor if a limit value is exceeded.

2. A device in accordance with claim 1, further comprising an acceleration sensor, the processor unit generating a shut-off signal or interruption signal for the process control system from the measurement signal of the acceleration sensor if a limit value is exceeded.

3. A process for the chromatographic detection of a substance, the process comprising the steps of:

providing a device comprising a test strip with a detection reagent, a measuring device housing with a test strip area, an optoelectronic scanning system for the test strip, a reservoir containing developer fluid for penetrating into the test strip to bring about a detection reaction and a process control system connected to an actuator for opening the reservoir and to the optoelectronic scanning system for exposure of the test strip to the developer fluid by controlling emptying of the reservoir to provide developer fluid from the reservoir to the test strip area and for analysis of the detection reaction with the optoelectronic scanning system;

supporting the test strip area, the reservoir and the optoelectronic scanning system with the housing;

exposing the test strip to the substance to be detected and inserting the test strip into the measuring device housing at the test strip area;

exposing the test strip to the developer fluid by emptying at least some of the developer fluid into the test strip area under the control of the process control system;

providing an inclination sensor that is supported by the device housing, the inclination sensor being connected to the process control system;

detecting, with an inclination sensor, the orientation of the device housing and the test strip area with respect to a direction of the force of gravity;

providing a processor unit connected to the process control system for generating a shut-off signal or interruption signal for the process control system; and interrupting or terminating an analysis operation by generating the shut-off signal or interruption signal for the process control system when a measured signal of the inclination sensor exceeds a preset limit value.

4. A device for the chromatographic detection of a substance, the device comprising:

a test strip provided with a detection reagent for detection of the substance;

an optoelectronic scanning system means for optoelectronically scanning the test strip to detect optically perceivable aspects of the test strip;

a reservoir containing developer fluid for penetration into the test strip to bring about a detection reaction;

a measuring device housing with a test strip area, said measuring device housing supporting said optoelectronic scanning system relative to said test strip area and supporting said reservoir in a position for distributing developer fluid to the test strip area;

a process control system for exposure of the test strip at the test strip area to the developer fluid and for analysis of the detection reaction with the optoelectronic scanning system;

a monitoring indicator with an inclination sensor for detecting the orientation of the measuring device housing with the test strip area with respect to a direction of the force of gravity and generating a measurement signal, the inclination sensor being connected to the process control system; and a processor unit for generating a shut-off signal or interruption signal for the process control system to interrupt or terminate an analysis operation by the process control system if a limit value of the relative position is exceeded.

5. A device according to claim 4, wherein the process control system is connected to an actuator for opening the reservoir for a controlled distribution of developer fluid to the test strip area.

* * * * *